United States Patent
Arai et al.

(10) Patent No.: US 12,234,485 B2
(45) Date of Patent: Feb. 25, 2025

(54) RESIN FILM FORMED BY SCAFFOLD MATERIAL FOR CELL CULTURE AND CONTAINER FOR CELL CULTURE

(71) Applicant: SEKISUI CHEMICAL CO., LTD., Osaka (JP)

(72) Inventors: Yuuhei Arai, Osaka (JP); Ryoma Ishii, Tokyo (JP); Hiroki Iguchi, Osaka (JP); Satoshi Haneda, Osaka (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 693 days.

(21) Appl. No.: 17/608,587

(22) PCT Filed: May 27, 2020

(86) PCT No.: PCT/JP2020/020891
§ 371 (c)(1),
(2) Date: Nov. 3, 2021

(87) PCT Pub. No.: WO2020/241675
PCT Pub. Date: Dec. 3, 2020

(65) Prior Publication Data
US 2022/0228127 A1    Jul. 21, 2022

(30) Foreign Application Priority Data
May 28, 2019   (JP) ................. 2019-099569

(51) Int. Cl.
*C12N 5/074*   (2010.01)

(52) U.S. Cl.
CPC ........ *C12N 5/0696* (2013.01); *C12N 2513/00* (2013.01); *C12N 2533/30* (2013.01)

(58) Field of Classification Search
CPC ............................................... C12N 2533/30
See application file for complete search history.

(56) References Cited

U.S. PATENT DOCUMENTS 4,537,790 A    8/1985  Horodniceanu et al.

FOREIGN PATENT DOCUMENTS

| JP | 2007137944 A | * | 6/2007 |
|----|--------------|---|--------|
| JP | 2009-201443  |   | 9/2009 |
| JP | 2009-273444  |   | 11/2009 |
| JP | 2015-67707   |   | 4/2015 |
| JP | 2017-70303   |   | 4/2017 |
| JP | 2017-201891  |   | 11/2017 |

OTHER PUBLICATIONS

JP 2007137944 A, machine translation. (Year: 2007).*
Fitzhugh et al. Relation of Composition of Polyvinyl Acetals to Their Physical Properties. I. Acetals of Saturated Aliphatic Aldehydes. Journal of Polymer Science 1952, 8;2:225-241. (Year: 1952).*
Zhang et al. Preparation and characterization of modified polyvinyl alcohol ultrafiltration membranes. Desalination 2006, 192:214- (Year: 2006).*
International Preliminary Report on Patentability and Written Opinion of the International Searching Authority issued Nov. 16, 2021 in International (PCT) Application No. PCT/JP2020/020891.
International Search Report (ISR) issued Aug. 18, 2020 in International (PCT) Application No. PCT/JP2020/020891.
Wakana Togami et al., "Effects of water-holding capability of the PVF sponge on the adhesion and differentiation of rat bone marrow stem cell culture", J. Biomed. Mater. Res. Part A, vol. 102A, pp. 247-253, 2014.
Akon Higuchi et al., "Long-term xeno-free culture of human pluripotent stem cells on hydrogels with optimal elasticity", Scientific Reports, 5, 18136, pp. 1-16, Dec. 14, 2015.

* cited by examiner

*Primary Examiner* — Christopher M Babic
*Assistant Examiner* — Jennifer S Spence
(74) *Attorney, Agent, or Firm* — Wenderoth, Lind & Ponack, L.L.P.

(57) ABSTRACT

Provided is a resin film having excellent cell extensibility in cell culture. The resin film formed of a scaffold material for cell culture containing a synthetic resin, the resin film having a compressive modulus of 5.5 GPa or more at a frequency of 1 Hz as measured using a nanoindenter device in ion-exchanged water in accordance with ISO14577-1 after being immersed in the ion-exchanged water at 37° C. for 24 hours.

11 Claims, 2 Drawing Sheets

[FIG. 1.]
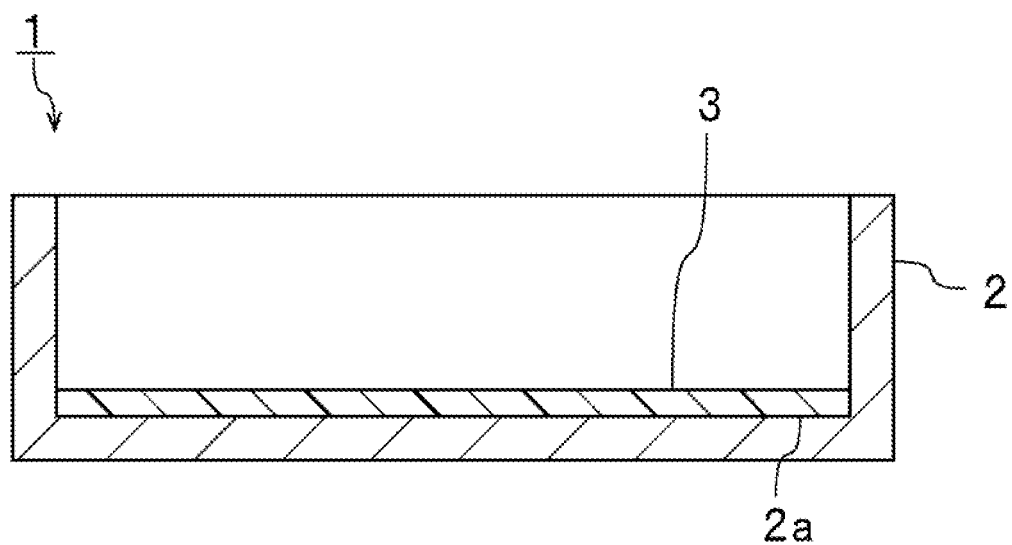
[FIG. 2.]
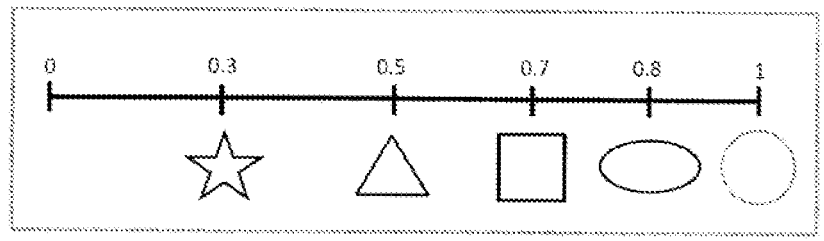

[FIG. 3.]
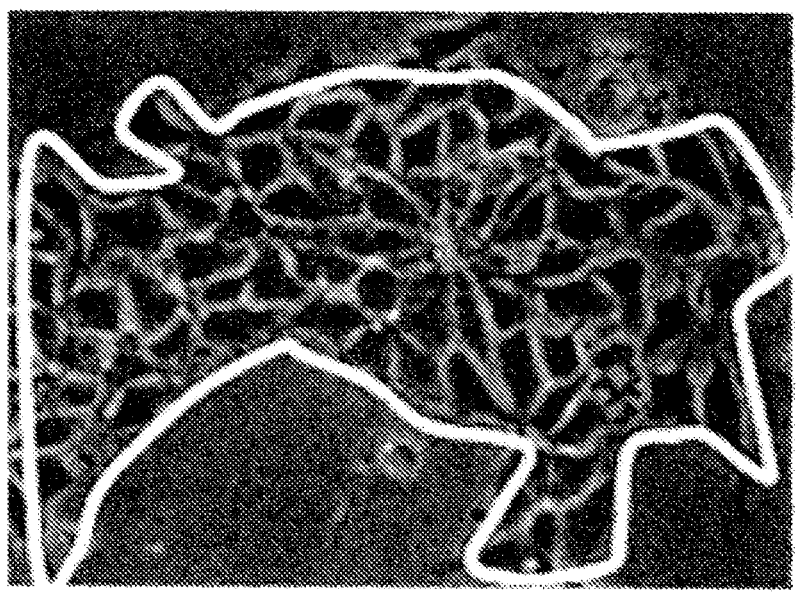
SF≒0.2
[FIG. 4.]
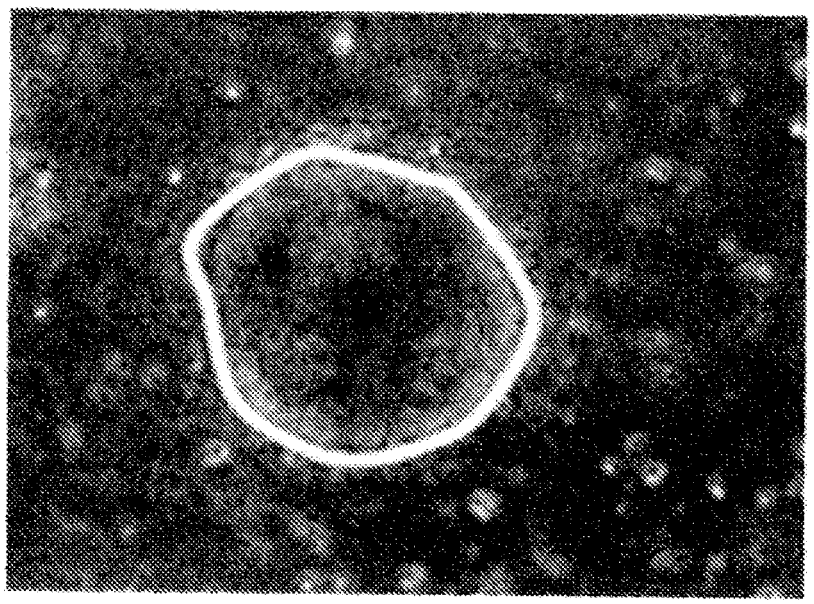
SF≒1

RESIN FILM FORMED BY SCAFFOLD MATERIAL FOR CELL CULTURE AND CONTAINER FOR CELL CULTURE

TECHNICAL FIELD

The present invention relates to a resin film formed of a scaffold material for cell culture used for culturing cells. The present invention also relates to a container for cell culture provided with the resin film.

BACKGROUND ART

Animal cells such as human, mouse, rat, pig, cattle and monkey cells axe used in research and development in academic fields, drug development fields, regenerative medicine fields and the like. As scaffold materials used for culturing an animal cell, adhesive proteins such as laminin and vitronectin, and natural polymer materials such as Matrigel derived from mouse sarcoma are used.

Furthermore, as shown in Non-Patent Document 1, and Patent Documents 1 and 2 below, scaffold materials obtained by using a synthetic resin are also known.

In Non-Patent Document 1 below, a poly (vinyl alcohol-vinyl acetal-itaconic acid) copolymer obtained by condensation reaction of fibronectin is used as a scaffold material used for culturing human iPS cells and ES cells.

Patent Document 1 below discloses a scaffold material in which DMAEMA is used as a cation, and acrylic acid, nucleic acid or heparin is used as an anion.

Patent Document 2 below discloses a scaffold material obtained by using a substrate for cell adhesion, which contains an arylsulfatase protein.

RELATED ART DOCUMENT

Non-Patent Document

Non-Patent Document 1: Sci. Rep. 5, 18136 Dec. 14, 2015

Patent Document

Patent Document 1: JP 2017-70303 A
Patent Document 2: JP 2009-201443 A

SUMMARY OF THE INVENTION

Problems to be Solved by the Invention

In culturing animal cells, a cell mass may be seeded on a scaffold material and cultured. As the scaffold material, a natural polymer material may be used. However, natural polymer materials are expensive. In addition, natural polymer materials axe naturally derived substances, so that there may be large variations, and safety issues due to animal-derived components.

Accordingly, various scaffold materials obtained by using synthetic polymers as described in Non-Patent Document 1, and Patent Documents 1 and 2 described above have been proposed.

However, the cell scaffold material described in Non-Patent Document 1 has a problem that cells contract and float when fibronectin is not contained, that is, when only a synthetic polymer is used.

In addition, the cell scaffold material described in Patent Document 1 has a problem that the material is highly hydrophilic due to its ionicity, causing cell mass contraction and cell aggregation.

Furthermore, the cell scaffold material described in Patent Document 2 has so high hydrophilicity that it easily swells. Accordingly, there is a problem that seeded stem cells are easily detached from the scaffold material during culture, so that the cell fixation is low.

An object of the present invention is to provide a resin film having excellent cell extensibility in cell culture, and a container for cell culture provided with the resin film.

Means for Solving the Problems

The resin film according to the present invention is a resin film formed of a scaffold material for cell culture containing a synthetic resin, in which the resin film has a compressive modulus of 5.5 GPa or more at a frequency of 1 Hz as measured using a nanoindenter device in ion-exchanged water in accordance with ISO14577-1 after being immersed in the ion-exchanged water at 37° C. for 24 hours.

In a specific aspect, the resin film according to the present invention has a contact angle in water of less than 145° and 100° or more in ion-exchanged water at 16° C.

In another specific aspect of the resin film according to the present invention, the number average molecular weight of the synthetic resin is $4.0 \times 10^4$ or more and $150 \times 10^4$ or less.

In yet another particular aspect of the resin film according to the present invention, the synthetic resin includes a polyvinyl alcohol derivative or a poly(meth)acrylic ester derivative.

In a more limited specific aspect of the resin film according to the present invention, the polyvinyl alcohol derivative is a polyvinyl acetal.

The container for cell culture according to the present invention includes a container main body and the resin film according to the present invention, and the resin film is arranged on the surface of the container main body.

Effect of the Invention

The resin film according to the present invention has a compressive modulus within the above-mentioned specific range. Therefore, the cell extensibility in cell culture can be enhanced.

BRIEF DESCRIPTION OF DRAWINGS

FIG. 1 is a front sectional view schematically showing a container for cell culture according to one embodiment of the present invention.

FIG. 2 is a schematic diagram showing the relationship between SF and the planar shape of a cell mass.

FIG. 3 is a photograph showing the state of extensibility when the SF is about 0.2 in Examples.

FIG. 4 is a photograph for explaining the cell extensibility when SF is about 1 in evaluation of Examples and Comparative Examples.

MODES FOR CARRYING OUT THE INVENTION

Hereinafter, a detailed description is made of the present invention.

The resin film according to the present invention is used for culturing cells. The resin film according to the present invention is formed of a scaffold material for cell culture containing a synthetic resin. In addition, the resin film according to the present invention has a compressive modulus of 5.5 GPa or more at a frequency of 1 Hz as measured using a nanoindenter device in ion-exchanged water in accordance with ISO14577-1 after being immersed in the ion-exchanged water at 37° C. for 24 hours.

The resin film according to the present invention has a compressive modulus within the above-mentioned specific range measured in ion-exchanged water after being immersed in ion-exchanged water at 37° C. for 24 hours. Therefore, when the resin is used for cell culture, the extensibility of cell mass can be enhanced.

The extensibility of cell mass can be evaluated by calculating the shape factor (SF).

Here, the shape factor (SF) is a shape evaluation coefficient of a region in a plan view of a cell mass after culturing cells. Calculation is performed by SF=4×π×(flat area of cell mass)/(length of outer periphery of cell mass)$^2$.

As shown in FIG. 2, when the SF is 1, the planar shape of cell mass is circular. The smaller the SF, the farther away from a circle, the less likely it is that a cell mass contracts, and the higher the cell extensibility. For example, in the case of the star shape shown in FIG. 2, the SF is 0.3, which can be said to be more excellent in extensibility than the case of the circle with SF=1.

Compressive Modulus

For the resin film according to the present invention, as described above, the compressive modulus at a frequency of 1 Hz as measured using a nanoindenter device in ion-exchanged water in accordance with ISO14577-1 after being immersed in the ion-exchanged water at 37° C. for 24 hours is within the above-mentioned specific range. The compressive modulus can be measured by the following method. First, a resin film formed of a scaffold material for cell culture is placed in a beaker filled with ion-exchanged water, and then the beaker is placed in a constant temperature bath at 37° C. and left for 24 hours. The immersed resin film is measured at a frequency of 1 Hz using a nanoindenter device (Triboindenter, manufactured by Hysitron) in ion-exchanged water in accordance with ISO14577-1. As to the method for analyzing the compressive modulus, calculation is performed according to the following formula.

$$\text{Compressive modulus}=\sqrt{\pi}\times(\text{load in elastic region}-\text{slope of displacement curve})/(2\times\sqrt{(\text{contact projected area})})$$

Here, the elastic region refers to a region where the load—the slope of displacement curve is constant. In addition, the contact projected area refers to an area where the indenter and a sample come into contact with each other.

For the indenter, Berkovich (triangular pyramidal type, tip diameter R: several hundred nm) can be used, and the indentation depth can be 50 nm.

When the compressive modulus at this time is 5.5 GPa or more, the cell extensibility in cell culture can be enhanced.

The compressive modulus is preferably more than 6.0 GPa, more preferably more than 6.5 GPa. When the compressive modulus is within the above-mentioned range, the cell extensibility can be more effectively enhanced.

The upper limit of the compressive modulus is not particularly limited, but is, for example, 15 GPa or less.

The compressive modulus can be adjusted within the above-mentioned range by, for example, adjusting the type and the number average molecular weight of the synthetic resin X described below. For example, as to the synthetic resin X described below, by selecting a resin having low hydrophilicity, increasing the number average molecular weight, forming a crosslinked structure between the molecules, etc., swelling in water is suppressed, so that it becomes easier to increase the compressive modulus.

Contact Angle in Water

The resin film according to the present invention preferably has a contact angle in water of less than 145° and 100° or more in ion-exchanged water at 16° C. When the contact angle in water is within the above-mentioned range, the cell extensibility can be more effectively enhanced.

The contact angle in water can be measured by the following method. First, a resin film formed of a scaffold material for cell culture is immersed in ion-exchanged water at 16° C. for 24 hours. Next, using a contact angle meter (DMo-601, manufactured by Kyowa Interface Science Co., Ltd.), 1 μl of air discharged from the syringe is brought into contact with the resin film. The contact angle in water can be measured by fitting the air contact angle by the tangent method.

The range of the contact angle in water is preferably less than 140°, and preferably 110° or more. When the contact angle in water is within the above-mentioned range, the cell extensibility can be furthermore effectively enhanced.

The contact angle in water can be reduced, for example, by increasing hydrophobic functional groups in the synthetic resin X described below. In addition, the contact angle in water can be increased by increasing hydrophilic functional groups in the synthetic resin X.

Synthetic Resin X

A scaffold material for cell culture used in the present invention contains a synthetic resin. This synthetic resin is hereinafter referred to as synthetic resin X.

The number average molecular weight of the synthetic resin X is preferably $4.0\times10^4$ or more, more preferably $5.0\times10^4$ or more, and preferably $150\times10^1$ or less, more preferably 100 ($10^4$ or less. When the number average molecular weight is the above-mentioned lower limit or more, the compressive modulus can be easily adjusted within the above-mentioned range. When the number average molecular weight is the above-mentioned upper limit or less, the cell extensibility in cell culture can be more effectively enhanced.

The number average molecular weight of the synthetic resin X can be measured by, for example, the following method. The synthetic resin X is dissolved in THF to prepare a 0.2% solution. Then, evaluation is performed using a gel permeation chromatography (GPC) measuring device (APC system, manufactured by Waters) under the following measurement conditions.

Column: HSPgel HR MB-M 6.0×150 mm, flow rate: 0.5 mL/min, column temperature: 40° C.

Injection volume: 10 μl, detector: RI, PDA, reference sample: polystyrene

The content of the synthetic resin X is preferably 90% by weight or more, more preferably 95% by weight or more, further preferably 97.5, by weight or more, particularly preferably 99% by weight or more, most preferably 100% by weight in the scaffold material for cell culture.

In addition to the synthetic resin X, the scaffold material for cell culture may contain a polymer such as a resin different from the synthetic resin X. The synthetic resin X is not particularly limited as long as the compressive modulus of the scaffold material for cell culture can be within the above-mentioned specific range.

The synthetic resin X includes polyolefin derivatives, polyether derivatives, polyvinyl alcohol derivatives, polyester derivatives, poly(meth)acrylic ester derivatives, epoxy resin derivatives, polyamide derivatives, polyimide derivatives, polyurethane derivatives, polycarbonate derivatives, cellulose derivatives, and polypeptide derivatives.

From the viewpoint of effectively exerting the effect of the present invention, the synthetic resin X is preferably polyvinyl alcohol derivatives or poly(meth)acrylic ester derivatives. The polyvinyl alcohol derivatives are a synthetic resin synthesized by using at least polyvinyl alcohol as a raw material. The poly(meth)acrylic ester derivatives are a synthetic resin synthesized by using at least an acrylic ester as a monomer.

The synthetic resin X preferably has a polyvinyl acetal skeleton or a poly(meth)acrylic ester skeleton. In this case, the synthetic resin X may be a resin having a polyvinyl acetal skeleton, a resin having a poly(meth)acrylic ester skeleton, or a resin having both a polyvinyl acetal skeleton and a poly(meth)acrylic ester skeleton.

From the viewpoint of effectively exerting the effect of the present invention, the synthetic resin X is preferably a resin having a polyvinyl acetal skeleton or a resin having a polyvinyl acetal skeleton and a poly(meth)acrylic ester skeleton. The synthetic resin X is preferably a resin having at least a polyvinyl acetal skeleton.

Synthetic Resin X Having Polyvinyl Acetal Skeleton

The scaffold material for cell culture preferably contains a synthetic resin X having a polyvinyl acetal skeleton.

In the specification, "synthetic resin X having a polyvinyl acetal skeleton" may be referred to as "polyvinyl acetal resin X".

Accordingly, the polyvinyl acetal resin X is a resin having a polyvinyl acetal skeleton.

The polyvinyl acetal resin X has an acetal group, an acetyl group and a hydroxyl group on the side chain.

The method for synthesizing the polyvinyl acetal resin X includes at least a step of acetalizing polyvinyl alcohol with an aldehyde.

The aldehyde used for acetalizing polyvinyl alcohol for preparing the polyvinyl acetal resin X is not particularly limited. Examples of the aldehyde include aldehydes having 1 to 10 carbon atoms. The aldehyde may have a chain aliphatic group, a cyclic aliphatic group or an aromatic group. The aldehyde may be a chain aldehyde or a cyclic aldehyde.

The type of the aldehyde includes formaldehyde, acetaldehyde, propionaldehyde, butyraldehyde, pentanal, hexanal, heptanal, octanal, nonanal, decanal, acrolein, benzaldehyde, cinnamaldehyde, perillaldehyde, formylpyridine, formylimidazole, formylpyrrole, formylpiperidine, formyltriazole, formyltetrazole, formylindole, formylisoindole, formylpurine, formylbenzimidazole, formylbenzotriazole, formylquinoline, formylisoquinoline, formylquinoxaline, formylcinnoline, formylpteridine, formylfuran, formyloxolane, formyloxane, formylthiophene, formylthiolane, formylthiane, formyladenine, formylguanine, formylcytosine, formylthymine and formyluracil. The aldehyde may be used alone or in combination of two or more.

The aldehyde is preferably formaldehyde, acetaldehyde, propionaldehyde, butyraldehyde or pentanal, more preferably butyraldehyde. Accordingly, the polyvinyl acetal skeleton is preferably a polyvinyl butyral skeleton. The polyvinyl acetal resin X is preferably a polyvinyl butyral resin.

The blending amount of the aldehyde can be appropriately set according to the desired amount of the acetal group. From the viewpoints of increasing the efficiency of acetalization reaction and easily removing unreacted aldehydes, the addition amount of the aldehyde is preferably 60 mol % or more, more preferably 65 mol % or more, and preferably 95 mol % or less, more preferably 90 mol % or less, with respect to 100 mol % of polyvinyl alcohol.

The number average molecular weight (Mn) of the polyvinyl acetal resin X is preferably 15,000 or more and preferably 1,000,000 or less. When the Mn is equal to or more than the above-mentioned lower limit and equal to or less than the above-mentioned upper limit, the strength of the resin film formed of the scaffold material for cell culture can be enhanced.

The degree of acetalization of the polyvinyl acetal resin X (degree of butyralization in the case of the polyvinyl butyral resin) is preferably 60 mol % or more, more preferably 65 mol % or more, and preferably 90 mol % or less, more preferably 85 mol %, or less. When the degree of acetalization is equal to or more than the above-mentioned lower limit, the cell fixation can be further enhanced, and the cells proliferate efficiently. When the degree of acetalization is equal to or less than the above-mentioned upper limit, the solubility in solvent can be better.

The glass transition temperature of the polyvinyl acetal resin X is preferably 40° C. or more, more preferably 45° C. or more, still more preferably 50° C. or more. By setting the glass transition temperature to the above-mentioned lower limit or more, the compressive modulus of the resin film can be more easily adjusted within the above-mentioned range. The upper limit of the glass transition temperature is not particularly limited, but may be, for example, 300° C. or less. The glass transition temperature can be measured using, for example, a differential scanning calorimeter.

The polyvinyl acetal resin X has a degree of acetylation (an amount of acetyl group) of preferably 0.0001 mol % or more and preferably 5 mol % or less.

The content rate of hydroxyl group (hydroxyl group content) of the polyvinyl acetal resin X is preferably 1 mol % or more, more preferably 10 mol % or more, and preferably 60 mol % or less, more preferably 60 mol % or less.

The degree of acetalization, the degree of acetylation, and the hydroxyl group content of the polyvinyl acetal resin can be measured by $^1$H-NMR (nuclear magnetic resonance spectrum).

The polyvinyl acetal resin X may be a polyvinyl acetal resin X synthesized using polyvinyl alcohol, or may be a copolymer of a polyvinyl acetal resin and a monomer. As such a monomer, a vinyl compound is suitably used. The vinyl compound includes ethylene, allylamine, vinylpyrrolidone, maleic anhydride, maleimide, itaconic acid, (meth) acrylic acid, vinylamine and (meth)acrylic ester. The vinyl compound may be used alone or in combination of two or more.

From the viewpoint of further enhancing the cell adhesion, the polyvinyl acetal resin X preferably has a Bronsted basic group or a Bronsted acidic group, more preferably has a Bronsted basic group. In other words, a part of the polyvinyl acetal resin X is preferably modified with a Bronsted basic group or a Bronsted acidic group, more preferably modified with a Bronsted basic group.

The Bronsted basic group is a generic term for a functional group that can receive a hydrogen ion H$^+$ from another substance. The Bronsted basic group includes amine-based basic groups such as a substituent having an imine structure, a substituent having an imide structure, a substituent having an amine structure, and a substituent having an amide structure.

The polyvinyl acetal resin X preferably has a structural unit having an imine structure, a structural unit having an imide structure, a structural unit having an amine structure, or a structural unit having an amide structure. In this case, the polyvinyl acetal resin X may have only one of these structural units, or may have two or more thereof.

The polyvinyl acetal resin X preferably has a structural unit having an imine structure. The imine structure refers to a structure having a C=N bond. The polyvinyl acetal resin X preferably has an imine structure on the side chain. In this case, the imine structure may be directly bonded to a carbon atom constituting the main chain of the polyvinyl acetal resin X, or may be bonded to the main chain via a linking group such as an alkylene group. Note that having the imine structure on the side chain includes having the imine structure on the graft chain of the polyvinyl acetal resin X. The structural unit having an imine structure includes a structural unit represented by the following formula (11) or (12).

[Chemical 1]

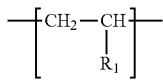

(11)

In the formula (11), $R_1$ represents a group having an imine structure.

[Chemical 2]

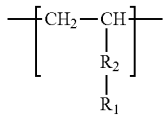

(12)

In the formula (12), $R_1$ represents a group having an imine structure, and $R_2$ represents an alkylene group. The alkylene group has preferably 1 or more, and preferably 12 or less, more preferably 5 or less carbon atoms. When the carbon number of the alkylene group is equal to or more than the above-mentioned lower limit and equal to or less than the above-mentioned upper limit, the strength of the resin film formed of the scaffold material for cell culture can be enhanced.

The alkylene group includes linear alkylene groups such as a methylene group, an ethylene group, a trimethylene group, a tetramethylene group, a pentamethylene group, a hexamethylene group, an octamethylene group and a decamethylene group, a branched alkylene groups such as a methyl methylene group, a methylethylene group, a 1-methylpentylene group and a 1,4-dimethylbutylene group, and cyclic alkylene groups such as a cyclopropylene group, a cyclobutylene group and a cyclohexylene group. The alkylene group is preferably a linear alkyl group such as a methylene group, an ethylene group, a trimethylene group or a tetramethylene group, more preferably a methylene group or an ethylene group.

$R_1$ in the formula (11) and $R_1$ in the formula (12) include groups represented by the following formula (13).

[Chemical 3]

(13)

In the formula (13), $R_3$ represents a hydrogen atom or a hydrocarbon group having 1 to 18 carbon atoms, and $R_4$ represents a hydrocarbon group having 1 to 18 carbon atoms.

The hydrocarbon group includes a saturated hydrocarbon group, an unsaturated hydrocarbon group and an aromatic hydrocarbon group. The hydrocarbon group may be one composed of only any one of a saturated hydrocarbon group, an unsaturated hydrocarbon group and an aromatic hydrocarbon group, or one in which two or more of them are used.

The saturated hydrocarbon group includes methyl, ethyl, n-propyl, isopropyl, n-butyl, iso-butyl, sec-butyl, tert-butyl, pentyl, hexyl, heptyl, 2-ethylhexyl, octyl, nonyl, decyl, undecyl, dodecyl, tridecyl, tetradecyl, pentadecyl and octadecyl groups. The saturated hydrocarbon group is preferably a methyl group, an ethyl group, an n-propyl group or an n-butyl group.

The aromatic hydrocarbon group includes phenyl, toluyl, xylyl, t-butylphenyl and benzyl groups.

It is preferable that the structural unit having an imine structure be a structural unit having the structure represented by the formula (11), and in the formula (13), $R_3$ be a hydrogen atom, a methyl group or an ethyl group, and $R_4$ be a methyl group, an ethyl group or a propyl group.

In the polyvinyl acetal resin X, the content rate of the structural unit having an imine structure is preferably 0.1 mol % or more, more preferably 1.0 mol % or more, and preferably 20.0 mol % or less, more preferably 1.5.0 mol % or less. When the content rate is equal to or more than the above-mentioned lower limit and equal to or less than the above-mentioned upper limit, the cell mass fixation can be further enhanced.

In the polyvinyl acetal resin X, the ratio of the content rate of the structural unit having an imine structure to the degree of acetalization (the content rate of the structural unit having an imine structure/degree of acetalization) is preferably 0.001 or more, preferably 0.5 or less. When the ratio (the content rate of the structural unit having an imine structure/degree of acetalization) is equal to or more than the above-mentioned lower limit and equal to or less than the above-mentioned upper limit, it is possible to enhance the strength of the resin film formed of the scaffold material for cell culture, and enhance the cell mass adhesion.

The polyvinyl acetal resin X preferably has a structural unit having an imide structure. The structural unit having an imide structure is preferably a structural unit having an imino group (—NH).

The polyvinyl acetal resin X preferably has the imino group on the side chain. In this case, the imino structure may be directly bonded to a carbon atom constituting the main chain of the polyvinyl acetal resin X, or may be bonded to the main chain via a linking group such as an alkylene group.

The polyvinyl acetal resin X preferably has a structural unit having an amine structure. The amine group in the amine structure may be a primary amine group, a secondary amine group, a tertiary amine group or a quaternary amine group.

The structural unit having an amine structure may be a structural unit having an amide structure. The amide structure refers to a structure having —C(=O)—NH—.

The polyvinyl acetal resin X preferably has the amine structure or the amide structure on the side chain. In this case, the amine structure or the amide structure may be directly bonded to a carbon atom constituting the main chain of the polyvinyl acetal resin X, or may be bonded to the main chain via a linking group such as an alkylene group.

Note that having the amine structure or the amide structure on the side chain includes having the amine structure or the amide structure on the graft chain of the polyvinyl acetal resin X.

From the viewpoint of enhancing the cell mass fixation, the amine group in the amine structure is preferably a primary amine group (—NH$_2$).

The structural unit having an amine structure is preferably a structure represented by the following formula (21).

[Chemical 4]

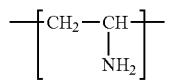

(21)

The structural unit having an amide structure is preferably a structure represented by the following formula (31).

[Chemical 5]

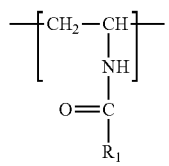

(31)

In the formula (31), $R_1$ represents a hydrogen atom or a hydrocarbon group having 1 to 10 carbon atoms. The hydrocarbon group includes an alkyl group, an alkenyl group, a cycloalkyl group and a cycloalkenyl group.

In the polyvinyl acetal resin X, the content rate of each structural unit having an amine structure or an amide structure is preferably 0.1 mol % or more, more preferably 0.5 mol % or more, and preferably 20 mol % or less, more preferably 10 mol % or less. When the content rate is equal to or more than the above-mentioned lower limit, additional properties can be improved. When the content rate is equal to or less than the above-mentioned upper limit, a polyvinyl acetal resin powder can be easily separated by the precipitation method.

In the polyvinyl acetal resin X, the content rate of the structural unit having an imine structure is preferably 0.5 mol % or more, more preferably 5 mol % or more, and preferably 99.5 mol % or less, more preferably 90 mol % or less, in a total of 100 mol % of the content rate of the structural unit having an imine structure and the content rate of the structural unit having an amine structure. In addition, in the polyvinyl acetal resin X, the content rate of the structural unit having an imine structure is preferably 0.5 mol % or more, more preferably 5 mol % or more, and preferably 99.5 mol % or less, more preferably 90 mol % or less, in a total of 100 mol % of the content rate of the structural unit having an imine structure and the content rate of the structural unit having an amide structure. When the content rate of the structural unit having an imine structure is equal to or more than the above-mentioned lower limit, the viscosity stability over time can be made sufficient. When the content rate of the structural unit having an imine structure is equal to or less than the above-mentioned upper limit, the cell adhesion can be further enhanced.

In the polyvinyl acetal resin X, the total content rate of the structural unit having an imine structure, the structural unit having an amine structure, and the structural unit having an imide structure is preferably 0.1 mol % or more, more preferably 1 mol % or more, and preferably 30 mol % or less, more preferably 10 mol % or less. In addition, in the polyvinyl acetal resin X, the total content rate of the structural unit having an imine structure, the structural unit having an amide structure, and the structural unit having an imide structure is preferably 0.1 mol % or more, more preferably 1 mol % or more, and preferably 30 mol % or less, more preferably 10 mol % or less. When the total content rate is equal to or more than the above-mentioned lower limit and equal to or less than the above-mentioned upper limit, the cell adhesion can be further enhanced.

The content rate of the structural unit having an imine structure, the content rate of the structural unit having an imide structure, the content rate of the structural unit having an amine structure and the content rate of the structural unit having an amide structure can be measured by $^1$H-NMR (nuclear magnetic resonance spectrum).

The Bronsted acidic group is a generic term for a functional group that can deliver a hydrogen ion H$^+$ to another substance.

The Bronsted acidic group includes a carboxyl group, a sulfonic acid group, a maleic acid group, a sulfinic acid group, a sulfenic acid group, a phosphoric acid group, a phosphonic acid group, and salts thereof. The Bronsted acidic group is preferably a carboxyl group.

The method for modifying the polyvinyl acetal resin X with the Bronsted acidic group includes a method for copolymerizing the polyvinyl alcohol with the itaconic acid or (meth)acrylic acid and a method for introducing a Bronsted acidic group into the side chain of the polyvinyl alcohol.

The method for producing the polyvinyl acetal resin X having a Bronsted basic group or a Bronsted acidic group is not particularly limited. For example, the polyvinyl acetal resin X having a structural unit having an imine structure can be produced by, for example, the following method (1), (2), (3) or (4). The polyvinyl acetal resin X may be an acetalized product of a polyvinyl alcohol having a structural unit having an amine structure or an amide structure.

(1) The monomer having an imine structure is copolymerized with vinyl acetate to prepare polyvinyl acetate. The obtained polyvinyl acetate is saponified to prepare polyvinyl alcohol. The resultant polyvinyl alcohol is acetalized by a conventionally known method.

(2) Polyvinyl alcohol having a structural unit having an amine structure or an amide structure is acetalized by a conventionally known method to introduce an imine structure.

(3) Polyvinyl alcohol having an imine structure obtained by post-modifying polyvinyl alcohol having a structural unit having an amine structure or an amide structure is acetalized by a conventionally known method.

(4) The polyvinyl acetal resin is modified to introduce an imine structure.

By the method (2) of the above (1) to (4), it is particularly preferable to prepare the polyvinyl acetal resin X having a structural unit having an imine structure.

In the above methods (1) to (4), the polyvinyl acetal resin X having a structural unit having an imine structure can be suitably obtained by a method including excessively adding an aldehyde or an acid catalyst used for acetalization.

In the method including excessively adding aldehyde, it is preferable to add 70 to 150 parts by weight aldehyde to 100 parts by weight a polyvinyl alcohol having a structural unit having an amine structure or an amide structure. Particularly, as the aldehyde, acetaldehyde, propionaldehyde, n-butyraldehyde, isobutyraldehyde, n-valeraldehyde and phenylaldehyde are preferable.

In the method including excessively adding an acid catalyst, it is preferable to add the acid catalyst in an amount of 0.5% by weight or more with respect to the whole weight. In addition, it is preferable to add 5.0 to 70.0 parts by weight acid catalyst to 100 parts by weight polyvinyl alcohol having a structural unit having an amine structure or an amide structure. Particularly, as the acid catalyst, hydrochloric acid, nitric acid, sulfuric acid and para-toluenesulfonic acid are preferable.

A known method can be used for the acetalization. The acetalization is preferably performed in an aqueous solvent, a mixed solvent of an organic solvent having compatibility with water, or an organic solvent. Examples of the organic solvent having compatibility with water include alcohol-based organic solvents. Examples of the organic solvent include alcohol-based organic solvents, aromatic organic solvents, aliphatic ester-based solvents, ketone-based solvents, lower paraffin-based solvents, ether-based solvents, amide-based solvents and amine-based solvents. The organic solvent may be used alone or in combination of two or more.

Examples of the alcohol-based organic solvents include methanol, ethanol, n-propanol, isopropanol, n-butanol and tert-butanol.

Examples of the aromatic organic solvents include xylene, toluene, ethylbenzene and methyl benzoate.

Examples of the aliphatic ester-based solvents include methyl acetate, ethyl acetate, butyl acetate, methyl propionate, ethyl propionate, methyl butyrate, ethyl butyrate, methyl acetoacetate and ethyl acetoacetate.

Examples of the ketone-based solvents include acetone, methyl ethyl ketone, methyl isobutyl ketone, cyclohexanone, methylcyclohexanone, benzophenone and acetophenone.

The lower paraffin-based solvents include hexane, pentane, octane, cyclohexane and decane.

The ether-based solvents include diethyl ether, tetrahydrofuran, ethylene glycol dimethyl ether, ethylene glycol diethyl ether and propylene glycol diethyl ether.

The amide-based solvents include N,N-dimethylformamide, N,N-dimethylacetamide, N-methylpyrrolidone and acetanilide.

The amine-based solvents include ammonia, trimethylamine, triethylamine, n-butylamine, di-n-butylamine, tri-n-butylamine, aniline, N-methylaniline, N,N-dimethylaniline and pyridine.

From the viewpoints of solubility in a resin and simplicity during purification, the organic solvent is preferably ethanol, n-propanol, isopropanol or tetrahydrofuran.

The acetalization is preferably performed in the presence of an acid catalyst. The acid catalyst is not particularly limited, but includes mineral acids such as sulfuric acid, hydrochloric acid, nitric acid and phosphoric acid, carboxylic acids such as formic acid, acetic acid and propionic acid, and sulfonic acids such as methanesulfonic acid, ethanesulfonic acid, benzenesulfonic acid and para-toluenesulfonic acid. The acid catalyst may be used alone or in combination of two or more. The acid catalyst is preferably hydrochloric acid, nitric acid or sulfuric acid, more preferably hydrochloric acid.

Synthetic Resin X Having Poly(Meth)Acrylic Ester Skeleton

The scaffold material for cell culture preferably contains a synthetic resin X having a poly(meth)acrylic ester skeleton.

In the specification, "synthetic resin X having a poly (meth)acrylic ester skeleton" may be referred to as "poly (meth)acrylic ester resin X".

Accordingly, the poly(meth)acrylic ester resin X is a resin having a poly(meth)acrylic ester skeleton.

The poly(meth)acrylic ester resin X can be obtained by polymerizing a (meth)acrylic ester or by polymerizing a (meth)acrylic ester and the above-mentioned other monomer.

The (meth)acrylic ester includes alkyl (meth)acrylic esters, cyclic alkyl (meth)acrylic esters, aryl (meth)acrylic esters, (meth)acrylamides, polyethylene glycol (meth)acrylates and phosphorylcholine (meth)acrylates.

The alkyl (meth)acrylic esters include methyl (meth) acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-octyl (meth)acrylate, isooctyl (meth)acrylate, 2-ethylhexyl (meth)acrylate, nonyl (meth)acrylate, isononyl (meth)acrylate, decyl (meth) acrylate, isodecyl (meth)acrylate, lauryl (meth)acrylate, stearyl (meth)acrylate and isotetradecyl (meth)acrylate.

The alkyl (meth)acrylic esters may be substituted with a substituent such as an alkoxy group having 1 to 3 carbon atoms and a tetrahydrofurfuryl group. Examples of such alkyl (meth)acrylic esters include methoxyethyl acrylate and tetrahydrofurfuryl acrylate.

The cyclic alkyl (meth)acrylic esters include cyclohexyl (meth)acrylate and isobornyl (meth)acrylate.

The aryl (meth)acrylic esters include phenyl (meth)acrylate and benzyl (meth)acrylate.

The (meth)acrylamides include (meth)acrylamide, N-isopropyl(meth)acrylamide, N-tert-butyl(meth)acrylamide, N,N'-dimethyl(meth)acrylamide, (3-(meth)acrylamidopropyl)trimethylammonium chloride, 4-(meth)acryloylmorpholine, 3-(meth)acryloyl-2-oxazolidinone, N-[3-(dimethylamino) propyl](meth)acrylamide, N-(2-hydroxyethyl) (meth)acrylamide, N-methylol(meth)acrylamide and 6-(meth)acrylamidohexanoic acid.

Examples of the polyethylene glycol(meth)acrylate include methoxy-polyethylene glycol(meth)acrylate, ethoxy-polyethylene glycol(meth)acrylate, hydroxy-polyethylene glycol(meth)acrylate, methoxy-diethylene glycol (meth)acrylate, ethoxy-diethylene glycol(meth)acrylate, hydroxy-diethylene glycol(meth)acrylate, methoxy-triethylene glycol(meth)acrylate, ethoxy-triethylene glycol(meth) acrylate and hydroxy-triethylene glycol(meth)acrylate.

The phosphorylcholine(meth)acrylates include 2-(meth) acryloyloxyethyl phosphorylcholine.

As the other monomer copolymerized with the (meth) acrylic ester, a vinyl compound is suitably used. The vinyl compound includes ethylene, allylamine, vinylpyrrolidone, maleic anhydride, maleimide, itaconic acid, (meth)acrylic acid, vinylamine and (meth)acrylic ester. The vinyl compound may be used alone or in combination of two or more.

Note that, in this specification, "(meth)acrylic" means "acrylic" or "methacrylic", and "(meth)acrylate" means "acrylate" or "methacrylate".

The number average molecular weight (Mn) of the poly (meth)acrylic ester resin X is preferably $60 \times 10^4$ or more and preferably $90 \times 10^4$ or less.

The poly(meth)acrylic ester resin X has a total of a structure derived from an alkyl(meth)acrylic ester, a structure derived from a cyclic alkyl(meth)acrylic ester, and a structure derived from an aryl(meth)acrylic ester contained in the constituent units of preferably 50% by weight or more, more preferably 60% by weight or more, further preferably 70% by weight or more. By setting the proportion of these structures derived from hydrophobic(meth)acrylic esters to the above-mentioned lower limit or more, the compressive modulus and the contact angle in water of the resin film can be more easily adjusted within the above-mentioned range.

The upper limit of the total of a structure derived from an alkyl(meth)acrylic ester, a structure derived from a cyclic alkyl(meth)acrylic ester, and a structure derived from an aryl(meth)acrylic ester contained in the constituent units of the poly(meth)acrylic ester resin X is not particularly limited, but may be 100% by weight or less.

The poly(meth)acrylic ester resin X may contain a structure derived from a polyfunctional (meth)acrylic ester in the constituent units. By containing a structure derived from a polyfunctional (meth)acrylic ester in the constituent units, the structure derived from the polyfunctional (meth)acrylic ester serves as a crosslinking point, which makes it easier to adjust the compressive modulus of the resin film within the above-mentioned range.

The proportion of the structure derived from the polyfunctional (meth)acrylic ester contained in the constituent units of the poly(meth)acrylic ester resin X is preferably 0.1% by weight or more and preferably 30% by weight or less.

The glass transition temperature of the poly(meth)acrylic ester resin X is preferably 40° C. or more, more preferably 45° C. or more, still more preferably 50° C. or more. By setting the glass transition temperature to the above-mentioned lower limit or more, the compressive modulus of the resin film can be more easily adjusted within the above-mentioned range. The upper limit of the glass transition temperature is not particularly limited, but may be, for example, 300° C. or less. The glass transition temperature can be measured using, for example, a differential scanning calorimeter.

Synthetic Resin X Having Polyvinyl Acetal Skeleton and poly(meth)acrylic ester Skeleton The scaffold material for cell culture preferably contains a synthetic resin X having a polyvinyl acetal skeleton and a poly(meth)acrylic ester skeleton. The synthetic resin X is preferably a composite resin having a polyvinyl acetal skeleton and a poly(meth)acrylic ester skeleton.

The synthetic resin X having a polyvinyl acetal skeleton and a poly(meth)acrylic ester skeleton can be synthesized by, for example, appropriately combining the above-mentioned method for synthesizing a polyvinyl acetal resin X and method for synthesizing a poly(meth)acrylic ester resin X.

The synthetic resin X having a polyvinyl acetal skeleton and a poly(meth)acrylic ester skeleton is preferably a synthetic resin X obtained by graft-copolymerizing the above-mentioned (meth)acrylic ester with the above-mentioned polyvinyl acetal resin.

The number average molecular weight (Mn) of the synthetic resin X having a polyvinyl acetal skeleton and a poly(meth)acrylic ester skeleton is preferably $60 \times 10^4$ or more and preferably $90 \times 10^4$ or less. When the Mn is equal to or more than the above-mentioned lower limit and equal to or less than the above-mentioned upper limit, the strength of the resin film formed of the scaffold material for cell culture can be enhanced.

The synthetic resin X may be crosslinked. The scaffold material for cell culture containing the crosslinked synthetic resin X can effectively suppress water swelling and increase the strength. By using a crosslinking agent, the synthetic resin X can be cross-linked.

The crosslinking agent includes polyalcohol, polycarboxylic acid, hydroxycarboxylic acid, metal soap and polysaccharides.

The polyalcohol includes ethylene glycol, propylene glycol, butanediol, pentanediol, hexanediol, heptanediol, octanediol, nonanediol, decanediol, dodecanediol, undecanediol, diethylene glycol, triethylene glycol, tetraethylene glycol, polyethylene glycol, catechol, pyrogallol, diboronic acid, methylenediboronic acid, ethylenediboronic acid, propylene diboronic acid, phenylenediboronic acid, biphenyldiboronic acid and bisphenol derivatives.

The polycarboxylic acid includes oxalic acid, malonic acid, succinic acid, glutaric acid, adipic acid, pimelic acid, suberic acid, azelaic acid, sebacic acid, phthalic acid and poly(meth)acrylic acid.

The hydroxycarboxylic acid includes glycolic acid, lactic acid, tartronic acid, glyceric acid, hydroxybutyric acid, malic acid, tartaric acid, cytomaric acid, citric acid, isocitric acid, leucic acid, mevalonic acid, pantoic acid, ricinoleic acid, ricineraidic acid, cerebronic acid, quinic acid, shikimic acid, hydroxybenzoic acid, salicylic acid, creosotic acid, vanillic acid, syringic acid, pyrocatechuic acid, resorcylic acid, protocatechuic acid, gentisic acid, orsellinic acid, gallic acid, mandelic acid, benzilic acid, atrolactic acid, melilotic acid, phloretic acid, coumaric acid, umbellic acid, caffeic acid, ferulic acid, sinapinic acid and hydroxystearic acid.

The metal soap includes salts of fatty acids such as stearic acid, lauric acid, ricinoleic acid and octylic acid with metals such as lithium, sodium, magnesium, calcium, barium, zinc and aluminum.

The polysaccharides include pectin, guar gum, xanthan gum, tamarind gum, carrageenan, propylene glycol, carboxymethylcellulose, amylose, amylopectin, glycogen, cellulose, chitin, agarose, carrageenan, heparin, hyaluronic acid, xyloglucan and glucomannanic acid.

Scaffold Material for Cell Culture

The scaffold material for cell culture constituting the resin film contains the synthetic resin X. From the viewpoints of effectively exerting the effect of the present invention and increasing the productivity, the content of the synthetic resin X in 100% by weight of the scaffold material for cell culture is preferably 90% by weight or more, more preferably 95% by weight or more, further preferably 97.5% by weight or more, particularly preferably 99% by weight or more, most preferably 100% by weight (total amount). Accordingly, the scaffold material for cell culture is most preferably the synthetic resin X. When the content of the synthetic resin X is equal to or more than the above-mentioned lower limit, the effect of the present invention can be more effectively exhibited.

The scaffold material for cell culture may contain components other than the synthetic resin X. The components include a polyolefin resin, a polyether resin, a polyvinyl alcohol resin, polyester, an epoxy resin, a polyamide resin, a polyimide resin, a polyurethane resin, a polycarbonate resin, polysaccharides, cellulose, polypeptide and synthetic peptide.

From the viewpoint of effectively exerting the effect of the present invention, the smaller the content of the components other than the synthetic resin X, the better. The content of the component in 100% by weight of the scaffold material for cell culture is preferably 20% by weight or less, more preferably 10% by weight or less, further preferably 5% by weight or less, particularly preferably 1% by weight or less, most preferably 0% by weight (not contained). Accordingly, the scaffold material for cell culture most preferably does not contain components other than the synthetic resin X.

The scaffold material for cell culture preferably does not substantially contain an animal-derived raw material. Since the scaffold material for cell culture does not contain an animal-derived raw material, it is possible to provide a scaffold material for cell culture that is highly safe and has little variation in quality in production. In addition, "does not substantially contain an animal-derived raw material" means that the amount of animal-derived raw material in the scaffold material for cell culture is 3% by weight or less. In the scaffold material for cell culture, the amount of animal-derived raw material is preferably 1% by weight or less, more preferably 0% by weight. In other words, the scaffold material for cell culture more preferably does not contain an animal-derived raw material at all.

Cell Culture Using Scaffold Material for Cell Culture

The scaffold material for cell culture according to the present invention is used for culturing cells. The scaffold material for cell culture according to the present invention is used as a scaffold for cells when the cells are cultured. Accordingly, the resin film formed of the scaffold material for cell culture of the present invention is used for culturing cells, and is also used as a scaffold for cells when the cells are cultured. It is particularly preferable that a cell mass be seeded on the resin film formed of the scaffold material for cell culture. The cell mass can be obtained by adding a cell detaching agent to a container for cell culture having confluent cells to detach the cells, and uniformly crushing the detached cells by pipetting. The cell detaching agent is not particularly limited, but is preferably an ethylenediamine/phosphate buffer solution. The size of the cell mass is preferably 50 μm to 200 μm. The resin film formed of the scaffold material for cell culture according to the present invention may be used for seeding and culturing cells having a form other than the cell mass.

The cells include animal cells such as human, mouse, rat, pig, bovine and monkey cells. In addition, the cells include somatic cells, such as stem cells, progenitor cells and mature cells. The somatic cell may also be cancer cells.

The mature cells include nerve cells, cardiomyocytes, retinal cells and hepatocytes.

The stem cells include mesenchymal stem cells (MSCs), iPS cells, ES cells, Muse cells, embryonal cancer cells, embryonic germ stem cells and mGS cells.

Form of Scaffold Material for Cell Culture

The resin film of the present invention is formed of the scaffold material for cell culture. The resin film is formed by using the scaffold material for cell culture. The resin film is preferably the scaffold material for cell culture in the form of a film. The resin film is preferably a film-like product of the scaffold material for cell culture.

In the specification, particles, fibers, a porous body or a film containing the scaffold material for cell culture are also provided. In this case, the form of the scaffold material for cell culture is not particularly limited, but may be particles, fibers, a porous body or a film. The particles, fibers, porous body or film may contain components other than the scaffold material for cell culture.

The film containing the scaffold material for cell culture is preferably used for plane culture (two-dimensional culture) of cells. In addition, particles, fibers or a porous body containing the scaffold material for cell culture are preferably used for three-dimensional culture of cells.

Carrier for Cell Culture

The present invention may be a carrier for cell culture, on the surface of which the resin film is arranged. The carrier for cell culture can be obtained by, for example, arranging the resin film on the surface of a carrier by coating or the like. The form of the carrier may be particles, fibers, a porous body or a film. In other words, the form of the carrier for cell culture may be particles, fibers, a porous body or a film. The carrier for cell culture may contain components other than the carrier and the resin film.

Container for Cell Culture

The container for cell culture according to the present invention includes a container main body and a resin film formed of the scaffold material for cell culture, and the resin film is arranged on the surface of the container main body.

FIG. 1 is a front sectional view schematically showing a container for cell culture according to one embodiment of the present invention.

The container for cell culture 1 includes a container main body 2 and a resin film 3 formed of the scaffold material for cell culture. The resin film 3 is arranged on the surface 2a of the container main body 2. The resin film 3 is arranged on the bottom surface of the container main body 2. Cells can be plane cultured by adding a liquid medium to the container for cell culture 1 and seeding cells such as a cell mass on the surface of the resin film 3.

The container main body may be provided with a second container main body such as a cover glass on the bottom surface of the first container main body. The first container main body and the second container main body may be separable. In this case, the resin film 3 formed of the scaffold material for cell culture may be arranged on the surface of the second container main body.

As the container main body, a conventionally known container main body (container) can be used. The shape and size of the container main body are not particularly limited.

The container main body includes a cell culture plate having one or more wells (holes) and a flask for cell culture. The number of wells in the plate is not particularly limited. The number of wells is not particularly limited, but examples thereof include 2, 4, 6, 12, 24, 48, 96 and 334. The shape of the well is not particularly limited, but includes perfect circle, ellipse, triangle, square, rectangle and pentagon. The shape of the bottom surface of the well is not particularly limited, but includes a flat bottom, a round bottom and irregularities.

The material of the container main body is not particularly limited, but includes resin, metal and inorganic materials. The resin includes polystyrene, polyethylene, polypropylene, polycarbonate, polyester, polyisoprene, cycloolefin polymer, polyimide, polyamide, polyamideimide, (meth)acrylic resin, epoxy resin and silicone. The metal includes stainless steel, copper, iron, nickel, aluminum, titanium, gold, silver and platinum. The inorganic material includes silicon oxide (glass), aluminum oxide, titanium oxide, zirconium oxide, iron oxide and silicon nitride.

Hereinafter, more detailed description is made of the present invention with reference to Examples and Comparative Examples. The present invention is not limited only to the Examples.

The followings were prepared as materials for a scaffold material for cell culture.

The content rate of structural unit in the obtained synthetic resin was measured by $^1$H-NMR (nuclear magnetic resonance spectrum) after dissolving the synthetic resin in DMSO-d6 (dimethylsulfoxide). Table 1 shows the content rate of each structural unit in the synthetic resin.

In Example 1, a polyvinyl acetal resin X1 (synthetic resin X1) was used.

Synthesis of Synthetic Resin X1

A reactor equipped with a stirrer was charged with 2700 mL of ion-exchanged water, 300 parts by weight of polyvinyl alcohol having an average degree of polymerization of 1700 and a degree of saponification of 97 mol %, followed by dissolution by heating with stirring to prepare a solution. To the resultant solution, 35% by weight hydrochloric acid was added as a catalyst such that the concentration of hydrochloric acid was 0.2% by weight. Then, the temperature was adjusted to 15° C., and 22 parts by weight of n-butyraldehyde was added with stirring. Then, 148 parts by weight of n-butyraldehyde was added to precipitate a polyvinyl butyral resin in the form of white particles. Fifteen minutes after the precipitation, 35% by weight hydrochloric acid was added such that the concentration of hydrochloric acid became 1.8% by weight, and then the mixture was heated to 50° C. and kept at 50° C. for 2 hours. Subsequently, the solution was cooled and neutralized, and then a polyvinyl butyral resin was rinsed with water, followed by drying to prepare a polyvinyl butyral resin (number average molecular weight 11×10$^4$, degree of acetalization (degree of butyralization) 65 mol %, hydroxyl group content 34 mol %, and degree of acetylation 3 mol %).

In Examples 2 to 5, polyvinyl acetal resins X2-X5 were used. In addition, in Examples 6 to 8, poly(meth)acrylic ester resins X6-X8 were used.

Polyvinyl Acetal Resin X2

The test was performed in the same manner as in Example 1, except for using a polyvinyl alcohol having an average degree of polymerization of 2500 and a degree of saponification of 97 mol %, and using acetaldehyde instead of n-butyraldehyde, to prepare a polyvinyl acetal resin (number average molecular weight 13×10$^4$, degree of acetalization 66 mol %, hydroxyl group content 33 mol %, and degree of acetylation 3 mol %).

Polyvinyl Acetal Resin X3

The test was performed in the same manner as in Example 1, except for using a polyvinyl alcohol having an average degree of polymerization of 850, a degree of saponification of 97 mol %, and a degree of amine modification of 2 mol %, to prepare a polyvinyl butyral resin (number average molecular weight 5×10$^4$, degree of acetalization 77 mol %, hydroxyl group content 20 mol %, degree of acetylation 1 mol %, and degree of amine modification 2 mol %).

Polyvinyl Acetal Resin X4

In tetrahydrofuran was dissolved 90 parts by weight of the same polyvinyl butyral resin as in Example 1 so as to be a 30% by weight solution, and was added 10 parts by weight of Coronate L (manufactured by Tosoh Corporation) as a crosslinking agent, followed by heating at 80° C. for 5 hours to prepare a polyvinyl butyral resin (number average molecular weight 100×10$^4$).

Polyvinyl Acetal Resin X5

In tetrahydrofuran was dissolved 90 parts by weight of the same polyvinyl butyral resin as in Example 1 so as to be a 30% by weight solution, and were added 0.1 parts by weight of Irgacure 184 as an initiator and 10 parts by weight of 1,6-hexanediol diacrylate, followed by graft polymerization to prepare a polyvinyl butyral resin (number average molecular weight 76×10$^4$).

Poly(meth)acrylic ester Resin X6

Twenty five parts by weight of butyl methacrylate, 70 parts by weight of methyl methacrylate, and 5 parts by weight of 1,6-hexanediol diacrylate were mixed to prepare a (meth)acrylic monomer solution. In the prepared (meth)acrylic monomer solution, 0.1 parts by weight Irgacure184 (manufactured by BASF) was dissolved, and the resultant mixture was applied onto a PET film. The coated product was irradiated with light having a wavelength of 365 nm at an integrated light amount of 2,000 mJ/cm$^2$ using a UV conveyor device "ECS301G1" manufactured by Eye Graphics Co., Ltd. at 25° C. to prepare a poly(meth)acrylic ester resin solution. The prepared poly(meth)acrylic ester resin solution was vacuum dried at 80° C. for 3 hours to prepare a poly(meth)acrylic ester resin. The number average molecular weight of the prepared poly(meth)acrylic ester resin was 60×10$^4$.

Poly(meth)acrylic ester Resin X7

In the same manner as for the poly(meth)acrylic ester resin X6, a poly(meth)acrylic ester resin X7 (number average molecular weight 78×10$^4$) was prepared, except for using 45 parts by weight of butyl methacrylate, 50 parts by weight of methyl methacrylate, and 5 parts by weight of 1,6-hexanediol diacrylate as the (meth)acrylic monomers.

Poly(meth)acrylic ester Resin X8

In the same manner as for the poly(meth)acrylic ester resin X6, a poly(meth)acrylic ester resin X8 (number average molecular weight 90×10$^4$) was prepared, except for using 65 parts by weight of butyl methacrylate, 30 parts by weight of methyl methacrylate, and 5 parts by weight of 1,6-hexanediol diacrylate as the (meth)acrylic monomers.

In addition, in Comparative Examples 1 to 4, acrylic resins Y1 to Y4 were used. In Table 1, the resin numbers X1 to X8 and Y1 to Y4 for these resins are listed.

Synthesis of poly(meth)acrylic ester Resin Y1

In the same manner as for the poly(meth)acrylic ester resin X6, a poly(meth)acrylic ester resin Y1 (number average molecular weight 20×10⁴) was prepared, except for using 95 parts by weight of butyl methacrylate and 5 parts by weight of 1,6-hexanediol diacrylate as the (meth)acrylic monomers.

Synthesis of poly(meth)acrylic ester Resin Y2

In the same manner as for the poly(meth)acrylic ester resin X6, a poly(meth)acrylic ester resin Y2 (number average molecular weight 12×10⁴) was prepared, except for using 60 parts by weight of butyl methacrylate and 15 parts by weight of lauryl acrylate as the (meth)acrylic monomers.

Synthesis of poly(meth)acrylic ester Resin Y3

In the same manner as for the poly(meth)acrylic ester resin X6, a poly(meth)acrylic ester resin Y3 (number average molecular weight 23×10⁴) was prepared, except for using 50 parts by weight of butyl methacrylate and 50 parts by weight of methacrylic acid as the (meth)acrylic monomers.

Synthesis of poly(meth)acrylic ester Resin Y4

In the same manner as for the poly(meth)acrylic ester resin X6, a poly(meth)acrylic ester resin Y4 (number average molecular weight 25×10⁴) was prepared, except for using 35 parts by weight of butyl methacrylate and 65 parts by weight of methacrylic acid as the (meth)acrylic monomers.

In Examples 1 to 8 and Comparative Examples 1 to 4, the above-mentioned resin was dissolved in 1-butanol to prepare a 5% by weight resin solution. To an area for culture of the container for cell culture was added dropwise 100 µL of the resin solution, followed by well familiarization. Next, the area for culture and the resin solution were allowed to stand at room temperature for 1 hour and then dried at 60° C. for 15 hours to prepare a container for cell culture having a resin film formed of a scaffold material for cell culture on the area for culture.

The compressive moduli of the resin films of Examples 1 to 8 and Comparative Examples 1 to 4 were measured as follows.

Measuring Method

First, the container for cell culture having a resin film formed of the scaffold material for cell culture was placed in a beaker filled with ion-exchanged water, and then the beaker was placed in a constant temperature bath at 37° C. and left for 24 hours. The water-immersed container for cell culture was taken out with ion-exchanged water remaining on the area for culture, and the compressive modulus of the resin film was measured using a nanoindenter device (Triboindenter, manufactured by Hysitron) in accordance with ISO14577-1. The compressive modulus was calculated according to the following formula.

$$\text{Compressive modulus} = \sqrt{\pi} \times (\text{load in elastic region} - \text{slope of displacement curve})/(2 \times \sqrt{(\text{contact projected area})})$$

Here, the elastic region refers to a region where the load-the slope of displacement curve is constant. In addition, the contact projected area refers to an area where the indenter and a sample come into contact with each other.

The indenter used was Berkovich (triangular pyramidal type, tip diameter R: several hundred nm), and the indentation depth was 50 nm.

Contact Angle in Water

A resin film formed of each of the scaffold materials for cell culture from the Examples and Comparative Examples was immersed in ion-exchanged water at 16° C. for 24 hours. Next, using a contact angle meter (DMo-601, manufactured by Kyowa Interface Science Co., Ltd.), 1 µL of air discharged from the syringe was brought into contact with the resin film. The contact angle in water was measured by fitting the air contact angle by the tangent method.

The values of the compressive modulus and the contact angle in water are shown in Table 1 below.

Evaluation of Cell Extensibility

Seeding and Culturing Stem Cells

To the obtained container for cell culture, 1 mL of phosphate buffered saline was added, and the mixture was allowed to stand for 1 hour in an incubator at 37° C. After removing the phosphate buffered saline in the dish, 1.0×10⁵ h-iPS cells 253G1 were seeded for performing culture in the presence of 1 mL of medium TeSR E8 (manufactured by STEM CELL) and 10 µM of ROCK-Inhibitor (Y27632) in an incubator at 37° C. under a $CO_2$ concentration of 5%.

Evaluation:

Evaluation of SF

As mentioned above, the shape factor (SF) was evaluated. In the evaluation, a phase contrast microscope (manufactured by Olympus Corporation, IX73) was used to plan view the cell mass. In the plan view of the cell mass, the SF value was calculated by $SF = 4 \times \pi \times (\text{flat area of cell mass})/(\text{length of outer periphery of cell mass})^2$. FIG. 3 is a photograph showing the planar shape of the cell mass when $SF \approx 0.2$, and FIG. 4 is a photograph showing the planar shape when $SF \approx 1$.

The results are shown in Table 1 below.

As is apparent from Table 1, in Comparative Examples 1 to 4, the SF value (shape factor) 24 hours after seeding was as extremely high as 0.7 to 0.9. On the other hand, in the resin films of Examples 1 to 8, the SF value was 0.4 or less, indicating that the cell extensibility was excellent. In particular, in Examples 1, 3, 4, and 5, the SF value was as low as 0.3 or less, indicating that the extensibility was further excellent.

TABLE 1

| | | | Ex. 1 | Ex. 2 | Ex. 3 | Ex. 4 | Ex. 5 | Ex. 6 | Ex. 7 |
|---|---|---|---|---|---|---|---|---|---|
| | | Resin number | X1 | X2 | X3 | X4 | X5 | X6 | X7 |
| Composition | Polyvinyl acetal resin | Degree of butyralization (mol %) | 65 | | 77 | 65 | 65 | | |
| | | Degree of acetalization (mol %) | | 66 | | | | | |
| | | Degree of acetylation (mol %) | 3 | 3 | 1 | 3 | 3 | | |
| | | Hydroxyl group content (mol %) | 34 | 33 | 20 | 34 | 34 | | |
| | | Degree of amine modification (mol %) | | 2 | | | | | |

TABLE 1-continued

| | | | | | | | | | |
|---|---|---|---|---|---|---|---|---|---|
| | Crosslinking agent | Coronate L (% by weight) | | | | | 10 | | |
| | Poly(meth)acrylic ester resin | Butyl methacrylate (% by weight) | | | | | | 25 | 45 |
| | | Lauryl acrylate (% by weight) | | | | | | | |
| | | Methyl methacrylate (% by weight) | | | | | | 70 | 50 |
| | | Methacrylic acid (% by weight) | | | | | | | |
| | | 1,6-Hexanediol diacrylate (% by weight) | | | | | 10 | 5 | 5 |
| | | Number average molecular weight [$\times 10^4$] | 11 | 13 | 5 | 100 | 76 | 60 | 78 |
| | | Glass transition point [° C.] | 90 | 110 | 80 | 100 | 95 | 79 | 61 |
| Evaluation of resin film | Compressive modulus [GPa] | After 24 hours in water | 8.99 | 5.90 | 7.20 | 9.50 | 9.25 | 8.50 | 7.50 |
| | Contact angle in water [°] | After 24 hours in water | 135 | 132 | 141 | 130 | 131 | 122 | 115 |
| Evaluation of cells | Cell extensibility | Shape factor (SF) 24 hours after seeding | 0.3 | 0.4 | 0.3 | 0.25 | 0.28 | 0.38 | 0.4 |

| | | | Ex. 8 | Comp. Ex. 1 | Comp. Ex. 2 | Comp. Ex. 3 | Comp. Ex. 4 |
|---|---|---|---|---|---|---|---|
| | Resin number | | X8 | Y1 | Y2 | Y3 | Y4 |
| Composition | Polyvinyl acetal resin | Degree of butyralization (mol %) | | | | | |
| | | Degree of acetalization (mol %) | | | | | |
| | | Degree of acetylation (mol %) | | | | | |
| | | Hydroxyl group content (mol %) | | | | | |
| | | Degree of amine modification (mol %) | | | | | |
| | Crosslinking agent | Coronate L (% by weight) | | | | | |
| | Poly(meth)acrylic ester resin | Butyl methacrylate (% by weight) | 65 | 95 | 80 | 50 | 35 |
| | | Lauryl acrylate (% by weight) | | | 15 | | |
| | | Methyl methacrylate (% by weight) | 30 | | | | |
| | | Methacrylic acid (% by weight) | | | | 50 | 65 |
| | | 1,6-Hexanediol diacrylate (% by weight) | 5 | 5 | 5 | | |
| | | Number average molecular weight [$\times 10^4$] | 90 | 20 | 12 | 23 | 25 |
| | | Glass transition point [° C.] | 45 | 23 | 15 | 97 | 128 |
| Evaluation of resin film | Compressive modulus [GPa] | After 24 hours in water | 6.58 | 4.51 | 1.23 | 0.39 | 0.12 |
| | Contact angle in water [°] | After 24 hours in water | 103 | 95 | 90 | 148 | 154 |
| Evaluation of cells | Cell extensibility | Shape factor (SF) 24 hours after seeding | 0.31 | 0.77 | 0.72 | 0.8 | 0.85 |

EXPLANATION OF SYMBOLS

1: Container for cell culture
2: Container main body
2a: Surface
3: Resin film

The invention claimed is:

1. A method of culturing a cell, comprising a step of culturing a cell on a resin film formed of a scaffold material containing a synthetic resin,
the resin film having a compressive modulus of 5.5 GPa or more and 15 GPa or less at a frequency of 1 Hz as measured using a nanoindenter device in ion-exchanged water in accordance with ISO14577-1 after being immersed in the ion-exchanged water at 37° C. for 24 hours, and
the resin film having a contact angle in water of less than 145° and 100° or more in ion-exchanged water at 16° C.

2. The method according to claim 1, wherein the resin film has a contact angle in water of less than 140° and 100° or more in ion-exchanged water at 16° C.

3. The method resin film according to claim 1, wherein the synthetic resin has a number average molecular weight of $4.0 \times 10^4$ or more and $150 \times 10^4$ or less.

4. The method according to claim 3, wherein the synthetic resin contains a polyvinyl alcohol derivative or a poly (meth) acrylic ester derivative.

5. The method according to claim 4, wherein the polyvinyl alcohol derivative is a polyvinyl acetal resin X,
the polyvinyl acetal resin X is a synthetic resin having a polyvinyl acetal skeleton.

6. The method according to claim 5, wherein the polyvinyl acetal skeleton is a polyvinyl butyral skeleton.

7. The method according to claim 5, wherein the polyvinyl acetal resin X has a structural unit having an imine structure, a structural unit having an imide structure, a structural unit having an amine structure, a structural unit having an amide structure or any combinations thereof.

8. The method according to claim 5, wherein the synthetic resin has a polyvinyl acetal skeleton and a poly (meth) acrylic ester skeleton.

9. The method according to claim 1, wherein the cell is a stem cell.

10. The method according to claim 9, wherein the stem cell is an iPS cell.

11. The method according to claim 1, wherein the resin film is arranged on a surface of a container main body.

* * * * *